US011202477B1

(12) United States Patent
Dawson

(10) Patent No.: US 11,202,477 B1
(45) Date of Patent: Dec. 21, 2021

(54) GARMENT FOR FEEDING TUBE

(71) Applicant: Thomas J. Dawson, Walnut Creek, CA (US)

(72) Inventor: Thomas J. Dawson, Walnut Creek, CA (US)

(*) Notice: Subject to any disclaimer, the term of this patent is extended or adjusted under 35 U.S.C. 154(b) by 0 days.

(21) Appl. No.: 16/057,468

(22) Filed: Aug. 7, 2018

Related U.S. Application Data

(60) Provisional application No. 62/542,653, filed on Aug. 8, 2017.

(51) Int. Cl.
| | |
|---|---|
| A41D 13/12 | (2006.01) |
| A41D 27/20 | (2006.01) |
| A41D 31/02 | (2019.01) |
| A61M 25/02 | (2006.01) |
| A41D 13/00 | (2006.01) |

(52) U.S. Cl.
CPC ....... *A41D 13/1245* (2013.01); *A41D 27/208* (2013.01); *A41D 31/02* (2013.01); *A61M 25/02* (2013.01); *A41D 2300/32* (2013.01); *A41D 2300/322* (2013.01); *A41D 2400/48* (2013.01); *A61M 2025/0206* (2013.01); *A61M 2202/0482* (2013.01)

(58) Field of Classification Search
CPC ............ A41D 13/1245; A41D 13/1281; A41D 13/1236; A41D 27/201; A41D 13/1272; A41D 27/20; A61M 2025/026; A61M 25/02; A61M 2025/0206; A61M 2025/0213; A61M 2039/085; A61M 2209/088; A61M 39/08
See application file for complete search history.

(56) References Cited

U.S. PATENT DOCUMENTS

| | | | | |
|---|---|---|---|---|
| 4,688,270 | A  * | 8/1987 | Denicola | A41D 13/1272 128/874 |
| 4,718,124 | A  * | 1/1988 | Sawicki | A41D 13/129 2/114 |
| 5,806,096 | A  * | 9/1998 | Pennington | A41B 13/08 2/102 |
| 6,477,710 | B1 * | 11/2002 | Ojoyeyi | A41D 13/1236 2/114 |
| 6,574,800 | B1 * | 6/2003 | Leger | A41D 13/1245 2/114 |
| 6,647,552 | B1 * | 11/2003 | Hogan | A41D 13/1245 2/114 |
| 7,073,204 | B1 * | 7/2006 | Boyles | A41D 13/1236 2/114 |
| 8,215,313 | B1 * | 7/2012 | Waltz | A61F 5/3715 128/873 |
| 8,607,366 | B2 * | 12/2013 | Austin | A61M 25/02 2/300 |

(Continued)

*Primary Examiner* — Robert H Muromoto, Jr.
(74) *Attorney, Agent, or Firm* — Knobbe Martens Olson & Bear LLP

(57) ABSTRACT

A garment for providing access to feeding tubes while the garment is being worn by a patient/individual. The garment includes a centralized access opening that is closable for portions of time and that provide access to a feeding tube or feeding tube mechanism that has been surgically implemented in a patient. The access opening may be located relatively central to the garment and can illustratively include additional fasteners that can secure a portion of the feeding tube to the garment.

16 Claims, 5 Drawing Sheets

(56) References Cited

U.S. PATENT DOCUMENTS

| | | | | |
|---|---|---|---|---|
| 8,690,835 | B1* | 4/2014 | Parris | A41D 13/1236 604/174 |
| 2004/0226073 | A1* | 11/2004 | McCullar | A41D 13/1245 2/114 |
| 2005/0102731 | A1* | 5/2005 | Beuk | A41D 13/1281 2/114 |
| 2006/0085890 | A1* | 4/2006 | Beuk | A41D 13/1281 2/114 |
| 2006/0253953 | A1* | 11/2006 | Williams | A41D 13/1272 2/69 |
| 2008/0000006 | A1* | 1/2008 | Ochoa | A41D 13/1236 2/114 |
| 2008/0221525 | A1* | 9/2008 | Manzano-Rivera | A61M 25/02 604/179 |
| 2009/0054844 | A1* | 2/2009 | Alyea | A41D 13/1245 604/179 |
| 2010/0205720 | A1* | 8/2010 | Ortega Astor | A41D 13/1281 2/247 |
| 2010/0242150 | A1* | 9/2010 | Trouillot | A41D 13/1245 2/114 |
| 2013/0133125 | A1* | 5/2013 | Mungaray | A41D 13/1245 2/114 |
| 2014/0025011 | A1* | 1/2014 | Murtha | A61M 39/08 604/180 |
| 2016/0050995 | A1* | 2/2016 | Bentley | A41D 27/201 2/114 |

\* cited by examiner

GARMENT FOR FEEDING TUBE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Generally described, individuals with medical conditions can be fitted with feeding tube. These individuals typically have to access the feeding tube throughout the day, including connecting a food source to the feeding tube external attachment mechanism. Use of a non-specialized garment can often require the individual to remove the garment or restrict access to the feeding tube if the garment remains worn

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure.

DETAILED DESCRIPTION

Generally described, the present application corresponds to a garment for providing access to feeding tubes while the garment is being worn by a patient/individual. More specifically, aspects of the present application correspond to a garment including a centralized access opening that is closable for portions of time and that provide access to a feeding tube or feeding tube mechanism that has been surgically implemented in a patient. Illustratively, the access opening of the garment may be opened and closed through the utilization of zippers, snaps, buttons, Velcro, and the like. The access opening may be located relatively central to the garment and can illustratively include additional fasteners that can secure a portion of the feeding tube to the garment. Utilization of the closure mechanisms, and additional covers, the garment can further not provide a ready indication that the individual wearing the garment has a feeding tube while facilitating access to the feeding tube or additional components.

Other approaches to garments for utilization in conjunction with some medical device, such as feeding tubes, are optimized for hospital stays or clinical visits in which access points are readily visible. Such approaches do not encourage wearing of the garment in more public settings. Additionally, some approaches provide access points in a manner, such as along the side of the garment, such that it does not facilitate the wearer of the garment from utilizing the access point. Rather, such access points are intended for providing access to clinicians, assistants or other third parties.

Although aspects of some embodiments described in the disclosure will focus, for the purpose of illustration, on the processing of specific types of garment configurations, one skilled in the relevant art will appreciate that the examples are illustrative only and are not intended to be limiting.

Figure 1:
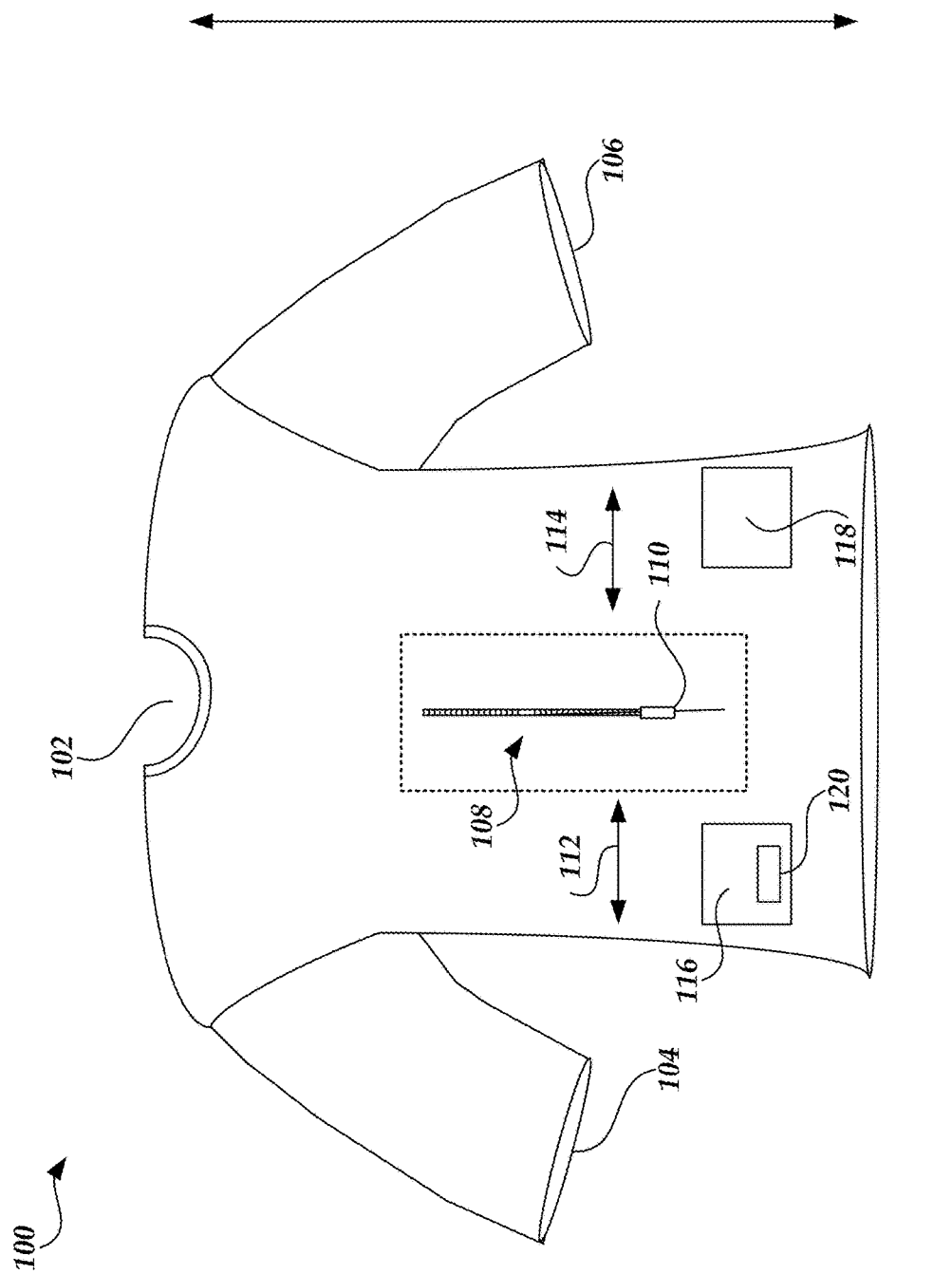
FIG. 1 is a front elevational view of a garment providing access to a feeding tube in accordance with an aspect of the present application.

FIG. 1 is a front elevational view of a garment 100 providing access to a feeding tube or feeding tube attachment mechanism in accordance with an aspect of the present application. As illustrated in FIG. 1, the garment 100 includes many of the traditional aspects of a garment worn by an individual, including an opening 102 for receiving the head and neck of the wearer along a top portion of the garment and two openings 104, 106 corresponding to arm sleeves that extend through the side portions of the garment. Although illustrated as a short sleeve garment, one skilled in the relevant art will appreciated that the garment may also incorporate long sleeves. Likewise, although illustrated as a collarless shirt (e.g., a t-shirt), one skilled in the art will appreciate that the garment may include various collar configurations, additional openings, or other features/accessories that can be found in garments, including features/accessories that may be directed to gender-specific preferences or styles.

With continued reference to FIG. 1, the garment 100 includes a centralized opening portion 108. The centralized opening portion 108 runs along a vertical axis relative to the garment 100. In the embodiment illustrated in FIG. 1, the centralized opening portion 108 is selectively closable, utilizing a securing mechanism, such as a zipper 110. The centralized opening portion 108 is illustratively of a sufficient size to facilitate the entry of the patient's hand and the exposure of a feeding tube mating mechanism. Additionally, the centralized portion 108 is of a length that is less than the length of the garment 100 such that it does not divide the garment. Additionally, the length of the centralized portion 108 can further facilitate the incorporation of traditional buttons, zippers or snaps along the collar of the garment 100 without interference. Illustratively, the length of the centralized opening portion can correspond to approximately six inches with a range from four inches to eight inches. However, one skilled in the relevant art will appreciate that the length of the centralized opening portion 108 may vary.

Additionally, the centralized opening is substantially central to the torso of the individual, such as substantially equidistant from the edges of the garment 100 along a horizontal axis as illustrated by 112 and 114. The garment 100 can further include optional one or more pockets 116, 118 that are operable to hold materials utilized to access the feeding tube (such as connectors), materials for cleaning or sterilizing the wearer or connectors, or materials utilized in providing the wearer with food, medication and the like. These pockets 116, 118 may be made of, at least in part, of a different material or processed specially, such as to provide water proof materials or having the same materials applied with a waterproofing coating or conditioner. Additionally, the pockets 116, 118 can include additional fasteners for closing/preservation, such as buttons, hooks and loops, Velcro, snaps and the like. Still further, the pockets 116, 118 can include labels 120 for identifying additional functionality for the wearer or service personnel. Such labels may be permanent or semi-permanent in nature and can further include color coding or symbols.

FIG. 2 is another front elevational view of a garment 200 providing access to a feeding tube or feeding tube attachment mechanism in accordance with an aspect of the present application. As illustrated in FIG. 2, the garment 200 includes many of the traditional aspects of a garment, including an opening 202 for receiving the head and neck of the wearer along a top portion of the garment and two openings 204, 206 corresponding to arm sleeves extending through the sides of the garment. As described above, although illustrated as a short sleeve garment, one skilled in the relevant art will appreciated that the garment 200 may also incorporate long sleeves. Likewise, although illustrated as a collarless shirt (e.g., a t-shirt), one skilled in the art will appreciate that the garment may include various collar configurations, additional openings, or other features/accessories that can be found in garments, including features/accessories that may be directed to gender-specific preferences or styles.

Figure 2A:
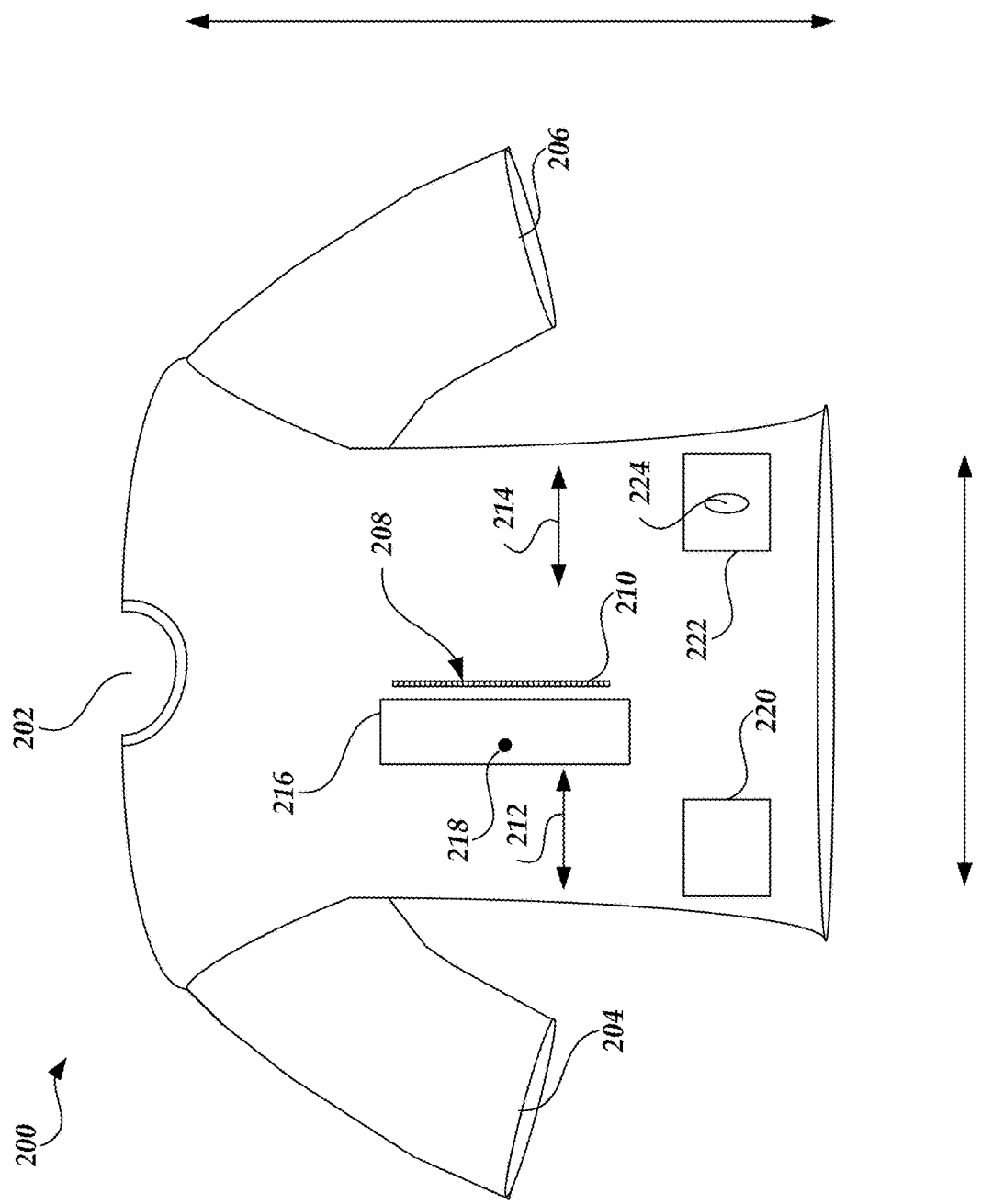
FIGS. 2A and 2B are front elevational views of a garment providing access to a feeding tube in accordance with an aspect of the present application.

With continued reference to FIG. 2A, the garment 200 includes a centralized opening portion 208. In this illustrative embodiment, the centralized opening portion 208 is substantially similar to the centralized opening portion 108 illustrated in FIG. 1 and runs along a vertical axis relative to the garment 200. Additionally, the centralized opening portion 208 is selectively closable, utilizing a securing mechanism, such as a zipper 210. The centralized opening portion 208 is illustratively of a sufficient size to facilitate the entry of the patient's hand and the exposure of a feeding tube mating mechanism and is substantially central to the torso of the wearer, such as substantially equidistant from the edges of the garment 100 as illustrated by 212 and 214. As described above, in one illustrative embodiment, the length of the centralized opening portion 208 is less than a length of the vertical access such that the garment 200 is not divided. As also illustrated in FIG. 2A, the garment 200 also includes a cover 216 or flap configured to substantially cover the centralized opening portion 208 in a closed position while exposing the centralized opening portion 208 in an open position.

Figure 2B:
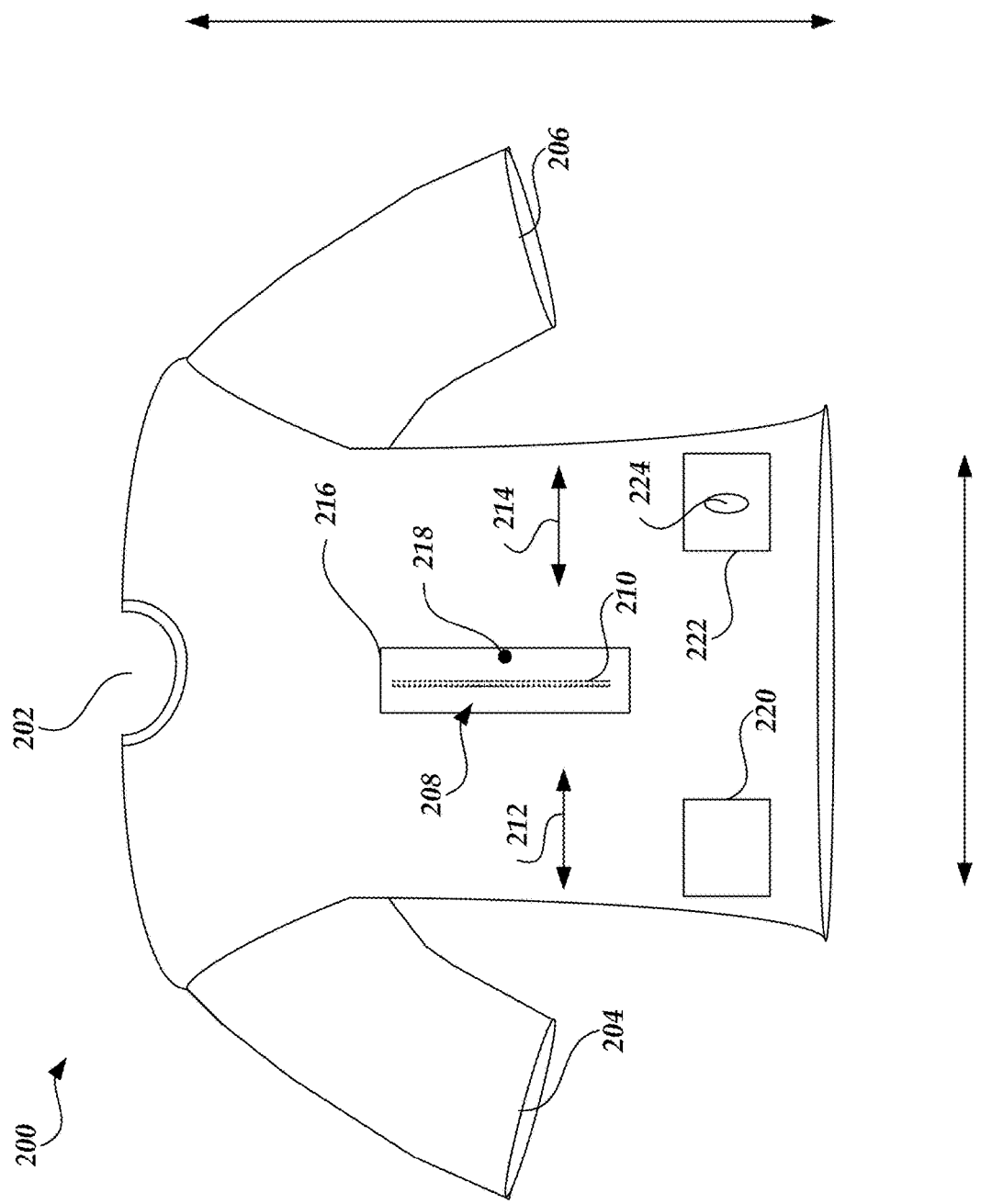

As illustrated in FIG. 2B, the cover 216 adheres to the garment 200 on one edge and overlaps with a substantial portion of the centralized opening portions 208 when folded over in the closed position. The centralized opening includes a fastener 218 for keeping the cover 216 adhered to the garment when the centralized opening portion 208 is closed. The fastener includes, but is not limited to, snaps, buttons, hook and button, Velcro and the like. The cover 218 also can be opened to not restrict (or minimally restrict) access to the feeding tube when the centralized opening is open. The cover 216 can be further diminished so as to resemble a pocket or other external feature of the garment 200 when in the closed position.

Similar to the garment 100 illustrated in FIG. 1, the garment 200 can further include optional one or more pockets 220, 222 that are operable to hold materials utilized to access the feeding tube (such as connectors), materials for cleaning or sterilizing the wearer or connectors, or materials utilized in providing the wearer with food, medication and the like. In one embodiment illustrated in FIG. 2, the pocket 220 can also include an internal opening 224 that provides a user with additional access points for the feeding tube or feeding tube attachment mechanism. Still further, one or more of the pockets 220, 22 may be made of, at least in part, of a different material or processed specially, such as to provide tear resistance or shield the wearer from sharp instruments. Additionally, the pockets 116, 118 can include additional fasteners for closing/preservation or labels for identifying additional functionality for the wearer or service personnel.

Figure 3:
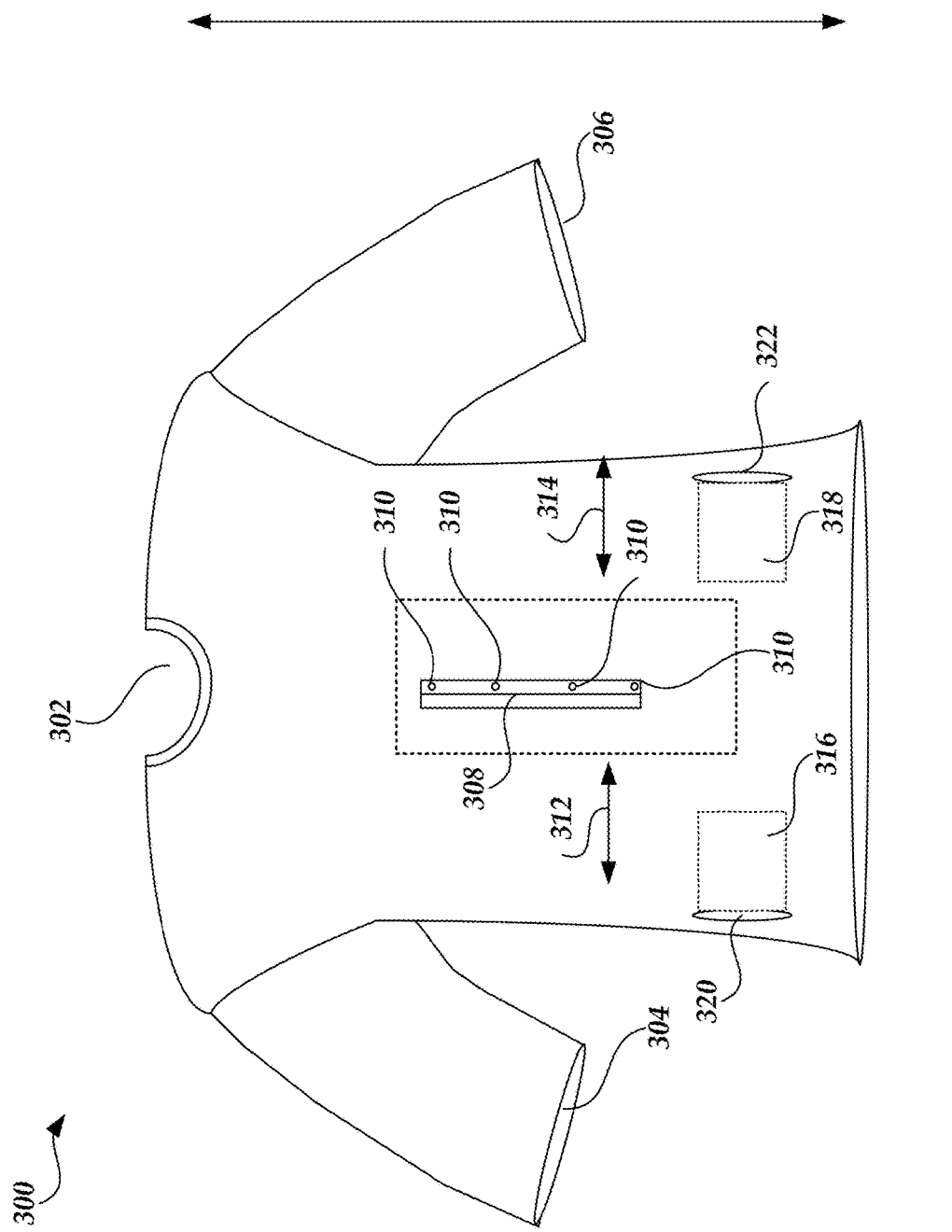
FIG. 3 is a another front elevational view of a garment providing access to a feeding tube in accordance with an aspect of the present application.

FIG. 3 is another front elevational view of a garment 300 providing access to a feeding tube or feeding tube attachment mechanism in accordance with an aspect of the present application. As illustrated in FIG. 3, the garment 300 includes many of the traditional aspects of a garment, including an opening 302 along a top portion of the garment 300 for receiving the head and neck of the wearer and two openings 304, 306 corresponding to arm sleeves extending through sides of the garment 300. Although illustrated as a short sleeve garment, one skilled in the relevant art will appreciated that the garment may also incorporate long sleeves. Likewise, although illustrated as a collarless shirt (e.g., a t-shirt), one skilled in the art will appreciate that the garment 300 may include various collar configurations, additional openings, or other features/accessories that can be found in garments, including features/accessories that may be directed to gender-specific preferences or styles.

With continued reference to FIG. 3, the garment 300 includes a centralized opening portion 308. In this illustrative embodiment, the centralized opening portion 308 is substantially similar to the centralized opening portions 108, 208 illustrated in FIGS. 1 and 2. The centralized opening portion 308 runs along a vertical axis relative to the garment 300. In this embodiment, the centralized opening portion 308 is selectively closable, utilizing a securing mechanism, such as a set of fasteners 310 corresponding to hook and loop buttons, snaps, plastic buttons and the like. The centralized opening portion 308 is illustratively of a sufficient size to facilitate the entry of the patient's hand and the exposure of a feeding tube mating mechanism and is substantially central to the torso of the wearer relative to a horizontal axis of the garment 300. The length of the centralized opening portion 308 is less than the length of the vertical axis such that the centralized opening portion does not subdivide the garment 300.

Similar to the illustrations of FIGS. 1 and 2, the garment 300 can further include optional one or more pockets 316, 318 that are operable to hold materials utilized to access the feeding tube (such as connectors), materials for cleaning or sterilizing the wearer or connectors, or materials utilized in providing the wearer with food, medication and the like. As described above, the pockets 316, 318 may be made of, at least in part, of a different material or processed specially. Additionally, the pockets 316, 318 can include additional fasteners for closing/preservation. Still further, as illustrated in FIG. 3, the pockets 316, 318 are internal pockets with openings 320, 322 in the side for providing additional access to the wearer or other user. The pockets 316, 318 may be configured with materials, additional stitching or treatment to prevent tearing, such as reinforcing the edges of the opening 320, 322. The pockets 316, 318 can also include labels or other coding to identify additional functionality or access to the wearer or other user.

Figure 4:
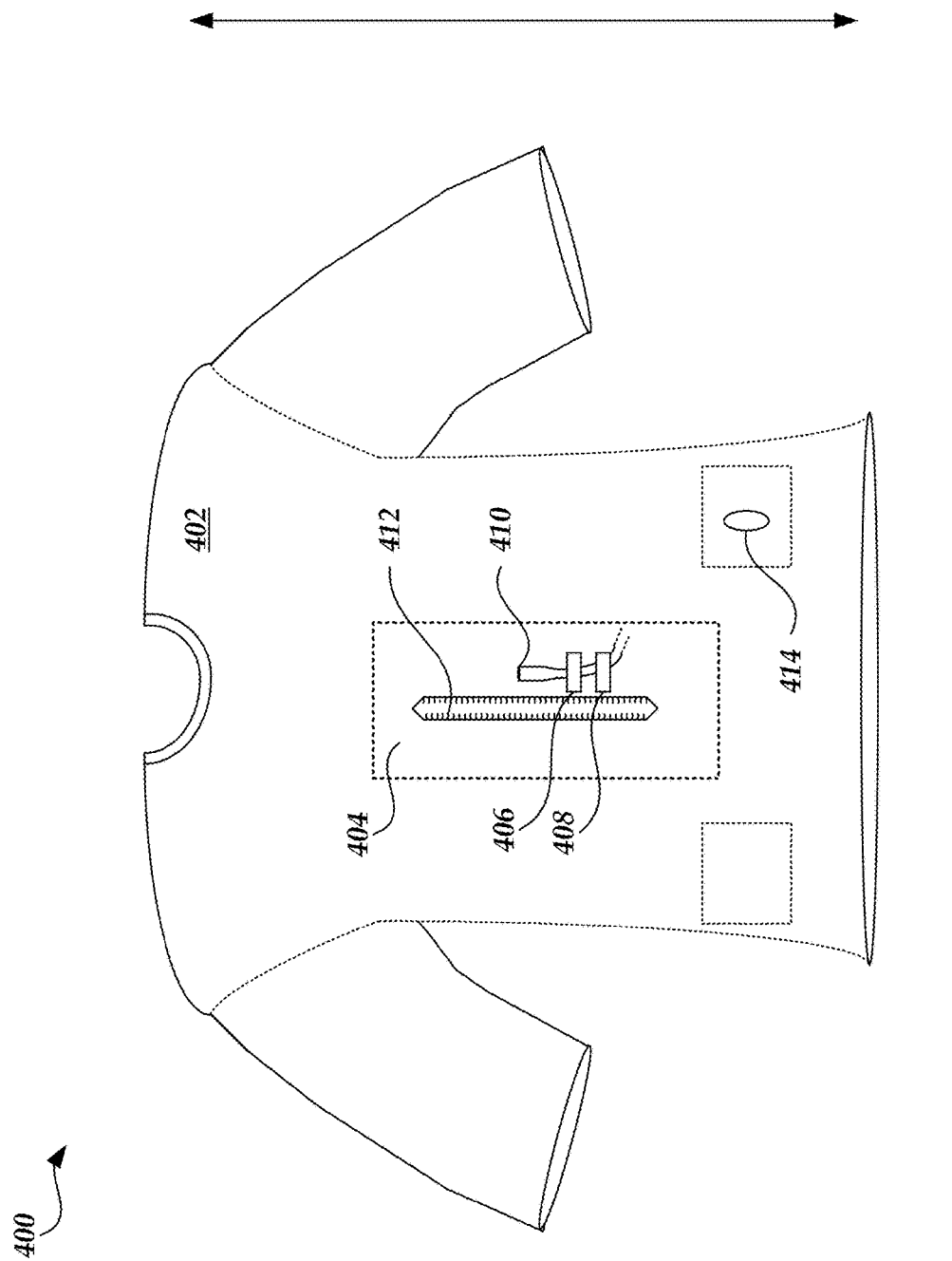
FIG. 4 is a front elevational view of an inside surface of a garment providing access to and securing a feeding tube in accordance with an aspect of the present application

FIG. 4 is a front elevational view of an inside surface 402 of a garment 400 providing access to and securing a feeding tube or feeding tube attachment mechanism in accordance with an aspect of the present application. As illustrated in FIG. 4, the garment 400 can include an internal layer or inside surface 402. The internal layer or inside surface 402 may be of the same material as an outer surface of the garment 400, which can correspond to any of the embodiments described with regard to FIGS. 1-3. The internal layer or inside surface 402 can further include a portion 404 that may be different from other portions of the inside surface, such as made with special materials or treated for a specific portion, such as resistivity to liquids, tear resistance or additional tackiness that prevents sliding of the feeding tube or feeding tube attachment mechanism. Portion 404 is illustrated generally in FIGS. 1 and 2 for illustration.

In some embodiments, adhered to the internal layer 402 are a set of fasteners 406, 408 that secure the feeding tube mechanism 410 to the garment. The fasteners can be made of Velcro, elastic, or other fabric and can further include magnetic mechanism for securing the feeding tube. Illustratively the set of fasteners are configured to be selectively releasable when the wearer accesses a feeding tube when the centralized opening 412 is accessed. Still further, the internal layer or insider surface 402 can include a light adherence material approximate to the fasteners 406, 408 that mitigates movement of the feeding tube mechanism. In conjunction with the embodiment illustrated in FIG. 2, the internal layer can also have an optional opening 414 corresponding to an external pocket.

What is claimed is:

1. A garment for use with a feeding tube, the garment comprising:
    a neck opening formed along a top portion of the garment;
    two arm sleeves with openings and extending through side portions of the garment;
    at least one pocket formed on a outer layer of a front portion of the garment, wherein the at least one pocket includes a substantially vertical internal opening on a side of the at least one pocket, the substantially vertical internal opening providing access to an inside layer of the front portion of the garment;
    a central opening portion on a front portion of the garment, the central opening portion having a vertical length sufficient to facilitate entry of a hand and exposure of a feeding tube attachment mechanism that is associated with the feeding tube and surgically implemented in a wearer of the garment, wherein the central opening portion is substantially equidistant along a horizontal axis between sides of the front portion of the garment, wherein the central opening portion includes a first fastener for interchangeably opening and closing the central opening portion, wherein the central opening portion extends less than the entire vertical axis of the garment and wherein the at least one pocket formed on the outer layer of the front portion of the garment is separate from the central opening portion on the front portion of the garment; and
    a second fastener located on an inside layer of the front portion, the at least one faster for securing the feeding tube attachment mechanism associated with the feeding tube to the inside layer of the garment.

2. The garment as recited in claim 1, wherein the fastener includes a zipper.

3. The garment as recited in claim 1, wherein the fastener includes a plurality of fasteners.

4. The garment as recited in claim 1, wherein the fastener includes a flap section adhered to the garment on a first side of the flap section and having a fastener on a second side of the flap section, wherein the fastener adheres the flap section to the garment in a closed position, wherein the flap section covers the central opening portion when in the closed position, and wherein the flap section exposes the central opening portion when in an open position.

5. The garment as recited in claim 1, wherein the at least one pocket includes at least one label, the label identifying one or more additional devices to be housed in the pocket.

6. The garment as recited in claim 1, wherein the at least one pocket is adapted to perform a function.

7. The garment as recited in claim 6, wherein the at least one pocket is adapted to be reinforced along an internal opening of the pocket to mitigate tearing.

8. The garment as recited in claim 6, wherein the at least one pocket is adapted to be reinforced to house additional devices including a sharp edge.

9. The garment as recited in claim 6, wherein the at least one pocket is adapted to be substantially waterproof.

10. The garment as recited in claim 1, wherein the inner layer has a portion adjacent to the fasteners to mitigate movement of the feeding tube attachment mechanism.

11. A garment for use with a feeding tube, the garment comprising:
    a neck opening formed along a top portion of the garment;
    two arm sleeves having openings and extending through side portions of the garment;
    at least one pocket formed on a outer layer of a front portion of the garment, wherein the at least one pocket includes a substantially vertical internal opening on a side of the at least one pocket, the substantially vertical internal opening providing access to an inside layer of the garment; and
    a central opening portion on a front portion of the garment, the central opening portion having a vertical length sufficient to facilitate entry of a hand and exposure of a feeding tube attachment mechanism that is associated with the feeding tube and surgically implemented in a wearer of the garment, wherein the central opening portion is substantially equidistant along a horizontal axis between sides of the front portion of the garment, wherein the central opening portion includes a first fastener for interchangeably opening and closing the central opening portion, wherein the central opening portion extends less than the entire vertical axis of the garment and wherein the at least one pocket formed on the outer layer of the front portion of the garment is separate from the central opening portion on the front portion of the garment.

12. The garment as recited in claim 11, wherein the first fastener includes one or more of a zipper, a hook and loop button, plastic button, or Velcro fastener.

13. The garment as recited in claim 11, wherein the first fastener includes a flap section adhered to the garment on a first side of the flap section and having a second fastener on a second side of the flap section, wherein the second fastener adheres the flap section to the garment in a closed position, wherein the flap section covers the central opening portion when in the closed position, and wherein the flap section exposes the central opening portion when in an open position.

14. The garment as recited in claim 11, wherein the at least one pocket is adapted to perform a function including reinforcement along an internal opening of the pocket to mitigate tearing.

15. The garment as recited in claim 11 further comprising at least one third fastener located on an inside layer of the front portion, the at least one third faster for securing the feeding tube attachment mechanism associated with the feeding tube to the insider layer of the garment.

16. The garment as recited in claim 15, wherein the inner layer has a portion adjacent to the first and third fasteners to mitigate movement of the feeding tube attachment mechanism.

* * * * *